(12) United States Patent
Stickel et al.

(10) Patent No.: US 11,406,440 B2
(45) Date of Patent: Aug. 9, 2022

(54) MEDICAL DEVICE AND METHOD FOR OPERATING A MEDICAL DEVICE

(71) Applicant: KARL STORZ SE & Co. KG, Tuttlingen (DE)

(72) Inventors: Axel Stickel, Tuttlingen (DE); Achim Sauter, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 191 days.

(21) Appl. No.: 16/863,325

(22) Filed: Apr. 30, 2020

(65) Prior Publication Data
US 2020/0352623 A1 Nov. 12, 2020

(30) Foreign Application Priority Data
May 6, 2019 (DE) ...................... 10 2019 111 644.9

(51) Int. Cl.
*A61B 18/12* (2006.01)
*A61B 18/00* (2006.01)
(52) U.S. Cl.
CPC .. *A61B 18/1206* (2013.01); *A61B 2018/0072* (2013.01); *A61B 2018/00708* (2013.01);
(Continued)
(58) Field of Classification Search
CPC ...... A61B 18/1206; A61B 2018/00642; A61B 2018/00648; A61B 2018/00672; A61B 2018/00678; A61B 2018/00708; A61B 2018/00714; A61B 2018/00791; A61B 2018/0072; A61B 2018/00767; A61B 2018/00779
See application file for complete search history.

(56) References Cited

U.S. PATENT DOCUMENTS 6,139,546 A * 10/2000 Koenig .............. A61B 18/1206
606/34
2003/0058985 A1 3/2003 Renz
(Continued)

FOREIGN PATENT DOCUMENTS

| DE | 10146894 C1 | 6/2003 |
| DE | 102011118265 A1 | 5/2013 |
| EP | 0671687 A2 | 9/1995 |

OTHER PUBLICATIONS

German Search Report for German Application No. 102019111644.9, dated Feb. 11, 2020.

*Primary Examiner* — Michael F Peffley
*Assistant Examiner* — Samantha M Good
(74) *Attorney, Agent, or Firm* — Jason H. Vick; Sheridan Ross, PC (57) ABSTRACT

A medical device equipped for switching the device on and off carries out at least one safety-relevant function in the operating state, using at least one operating parameter with a set target value. In order to ensure a reliable function of the device and not disturb a medical treatment, the device performs a first self-diagnosis following switch-on and before reaching an operating state and performs a second self-diagnosis following switch-off and before terminating the operating state, during which self-diagnoses the same operating parameter of the device is checked in each case for deviation from the target value. The technology also relates to a corresponding method for operating a medical device.

20 Claims, 2 Drawing Sheets

(52) U.S. Cl.
CPC ............ *A61B 2018/00714* (2013.01); *A61B 2018/00744* (2013.01); *A61B 2018/00767* (2013.01); *A61B 2018/00898* (2013.01)

(56) References Cited

U.S. PATENT DOCUMENTS

2008/0147136 A1 6/2008 Zhou et al.
2013/0118489 A1 5/2013 Wagener et al.
2015/0261637 A1 9/2015 Ouchi

* cited by examiner

MEDICAL DEVICE AND METHOD FOR OPERATING A MEDICAL DEVICE

CROSS REFERENCE TO RELATED APPLICATIONS

This application claims the benefit under 35 U.S.C. 119(a) to German Patent Application No. 10 2019 111 644.9, filed May 6, 2019, the disclosure of which is incorporated herein by reference in its entirety

SUMMARY

The technology relates to a medical device with means for switching the device on and off, in order to activate the device and put it into an operating state and in order to deactivate it and terminate an operating state. The device performs a self-diagnosis upon switch-on.

Medical devices fulfill multifaceted functions in medicine. Thus, they are used, inter alia, to provide liquids and gases, light, current or heat, to supply connected medical instruments or to provide open-loop and closed-loop control for instruments, further devices and components. Known medical devices include suction pumps and flushing pumps, light sources, generators for electrosurgery, but also camera control units, insufflators or devices for navigated surgery. What is common to all is that they provide various functions for the medical user, which are required for successful treatment of patients. To this end, medical devices are frequently connected to instruments, other components such as input devices and monitors and among themselves and interchange signals, current or other supply means. Here, the function of the devices has direct effect on the desired application and on the patient and therefore represents a safety-relevant aspect. Therefore, medical devices are frequently equipped with redundant sensors and other means, which facilitate reliable operation of the devices and identify occurring malfunctions. All safety-relevant functions of a device are monitored continuously during operation. It is usual for a determined malfunction or an operating parameter of a device measured outside of given target values to be automatically communicated to the user and, in extremis, for the further operation of the device to be prevented. Here, a balance must be struck between the greatest possible patient safety and the requirement of a frictionless course of a treatment, for example an operation. Thus, constant availability of a function of a medical device may be necessary for the medical intervention, precluding an interruption of the operation. A function of a device not meeting the requirements should therefore be determined in timely fashion and with great reliability, and, simultaneously, be communicated to a user at the right time.

To this end, US2008/0147136A1 has disclosed, for example, the practice of letting a medical device regularly perform self-diagnoses in the deactivated state, i.e., while it is not in operation. By way of example, these may occur after the expiry of a certain amount of time. This ensures that a device works properly when its use is intended and possibly occurring deviations are already determined prior to the application, for example in order to be able to reset or repair the device.

The disadvantage of this process is that the device needs to be continuously connected to a power source to this end. This known type of self-diagnosis is particularly suitable for mobile battery-operated devices that are only used occasionally, such as defibrillators, for example.

The specified prior art moreover describes a known solution, in which a self-diagnosis is performed during the switch-on process.

However, a negative result, such as a malfunction or an operating parameter measured outside of specified values, leads to possible delays or even interruptions after the switch-on, which could interfere with the treatment of a patient.

It is therefore an object of the present technology to provide a medical device and a method for operating a medical device, which reliably identifies occurring malfunctions and deviations in operating parameters of the device and which moreover increases the probability of the device being operationally available at the time of application. In the process, the aforementioned disadvantages should be avoided.

According to the technology, the object is achieved by a medical device as claimed in claim 1 and a method as claimed in claim 13.

A medical device comprises means for switching the device on and off, wherein a switch-on activates the device and puts it into an operating state and a switch-off deactivates the device and terminates the operating state. In the operating state, the device carries out at least one safety-relevant function, with at least one operating parameter with a set target value being used to this end. The device performs a first self-diagnosis following switch-on and before reaching the operating state and performs a second self-diagnosis following switch-off and before terminating the operating state, during which self-diagnoses the same operating parameter of the device is checked in each case for deviation from the target value.

As described above, a medical device provides various functions for patients and users. The device can be an apparatus, housed in a single housing, with components for fulfilling the function, or else it can be divided among a plurality of components. It may comprise input devices, displays, lines for current, signals or fluids (liquids or gases). The device can have a controller. Devices of the same and different type can be interconnected, can interchange signals, and can be controlled together by one of the devices or else centrally by a control unit. Input devices and displays can be attached directly to the device housing or can be set up separately therefrom and can be connected via lines. By way of example, input devices include keyboards, operating buttons, touchscreens, foot pedals or else microphones for voice control.

By way of example, medical devices include suction and/or flushing pumps, which are configured to fulfill a flushing or suction function. They provide the user and the patient with liquid for flushing the site or suck away blood, liquid or smoke from the latter. To this end, a pump is directly connected via fluid lines to the patient or to a channel of a medical instrument such as an endoscope or an electrosurgical instrument used on the patient.

Here, the device has switches or other input devices as means for switching the device on and off in order to switch the device on and off. This can be implemented directly on the device via a switch, via a touchscreen, speech input into a microphone or else via a switch on a central control unit or another separate input device. A plurality of devices can be activated or deactivated at the same time. The switches or input devices could also be provided on the medical instrument and control the device. A switch can be a pressure switch, lever or any other component for switching known to a person skilled in the art. Additionally, switch-on can be implemented at a certain time or on the basis of the operating state of another device. By way of example, a pump for sucking smoke or an associated tube constriction valve can be activated and deactivated on the basis of the activity of an RF generator or RF instrument.

Below, switch-on and switch-off denote triggering the switching on and switching off process, i.e., triggering an activation or deactivation in which the device is converted into an operating state or said operating state is terminated. This can also include booting or shutting down a device controlled by software. The switch-on or switch-off is a prompt for the device or its controller to activate or terminate the operating state. The switch-on and switch-off can also relate to connecting a power supply unit of the device to a power supply. Alternatively, the device is in an electrical standby state, from which it is awoken by the switch-on or to which it is returned by the switch-off.

A device is in the operating state if it is ready to carry out the function provided by the device. This can be implemented automatically or following a further prompt or input by the user.

In the present case, a safety-relevant function is understood to mean a function which is fulfilled or provided by the device and which can impair the safety of a patient or an operator of the device. Virtually all functions will be safety relevant in medical devices, with individual functions possibly having greater relevance to the safety than others. Thus, the provision of current for an electrosurgical application represents a very safety-relevant function since the current constitutes a danger to the patient and user. This function is subject to correspondingly strict restrictions and specifications by target values and structural measures in the device in order to avoid any risk to the patient and user.

Likewise, the provision of insufflation gas by a device such as an insufflator, for example, represents a safety-relevant function since the gas is supplied directly to the patient and excess pressure can damage the patient.

In order to control and monitor the function of the device, the function is based on at least one operating parameter which co-defines and facilitates the function of the device. By way of example, this can be a voltage, a current intensity, a pressure, a temperature, a flow of a fluid such as CO2 gas or water, a luminous flux or an amount of energy provided. A voltage can be a supply voltage of the device or of a component of the device, or this may relate to a voltage between components in the device.

The present technology relates, in particular, to the mains-operated devices, i.e., devices which are connected, for example via a power supply unit, to the power grid and which are only operated by mains current. In particular, they do not have a mobile power source such as a battery.

A single target value or value range of target values are assigned to the operating parameter; these represent the preferred value for the operation of the device and the provision of the function. The target value can be programmed into the device, into parts of the device or into device software, or it can be set by the user via input means. The target value can depend on the medical application, on the employed materials, on components or else on ambient conditions such as an ambient temperature. Optionally, the device could have a controller which adapts the target value on the basis of other operating parameters or the desired application. The target value for the operating parameter can be a different value at the time of the first self-diagnosis than at the time of the second self-diagnosis.

In order now to ensure the reliable operation of the device, the device performs a first self-diagnosis following switch-on and before reaching the actual operating state. In the present case, this is understood to mean that the device comprises sensors or other components such as an electrical circuit, which measures or captures the actual value of the operating parameter or parameters and compares this to the target value. The intention is to identify a deviation of the measured value from the target value. All operating parameters or only individual operating parameters can be checked.

Likewise, the device performs a second self-diagnosis following switch-off and before the actual termination of the operating state. This can be implemented just like the first self-diagnosis. In any case, a certain operating parameter is measured in both self-diagnoses and the captured value is compared to the target value. A deviation is present if the measured value of the operating parameter does not correspond to the target value or the range of target values. For the purposes of controlling the device, triggering and performing the self-diagnosis and/or evaluating and comparing the measured values, the device can have a controller in a manner known per se. By way of example, the latter comprises at least one microprocessor and a memory. Alternatively, the evaluation is implemented in another apparatus that is signal-connected to the device.

A deviation from a target value of an operating parameter may have various causes. Thus, an advanced service life and wear of components and component parts of the device may lead to deviations. Additionally, an exposure of electronic and other components to high temperatures, the dirtying of mechanical components or improper handling of the device by operating staff leads to desired values of voltage, provided power, air flow or the like no longer corresponding to the target values. Here, a deviation from a target value is initially only a quantitatively captured result. Then, depending on the extent and assessment, it may be safety relevant or even indicate a malfunction of the device. However, it may also have only a negligible size and arise, for example, on account of the heating of the device during running operation and then be captured during the second self-diagnosis.

Likewise, a deviation may arise from the influence of high temperature or other ambient conditions on the measurement sensors. That is to say, the captured deviation of an operating parameter might in fact not be due to the operating state of the device but may be due to the sensor which captures the parameter and supplies incorrect or deviating measured values on account of non-ideal ambient conditions. The second self-diagnosis can also capture this and take this into account, especially if the deviating behavior of the sensor due to the ambient temperature or other ambient conditions is known.

Performing two self-diagnoses at different times, one after switch-on and one after switch-off, increases the reliability and the quality and meaningfulness of the measurement since, firstly, a plurality of measurements are performed and, secondly, different phases during the operation of the device are taken into account. A device heated by operation has a different behavior to a device that has only just been switched on.

Each switch-on of the device triggers the first self-diagnosis and each switch-off triggers the second self-diagnosis. Thus, the self-diagnoses are performed by the device during all switching on and off processes, further increasing the reliability.

Moreover, two self-diagnoses open up various possibilities for comparing the values and deviations, for processing these and for drawing conclusions therefrom about the actual state of the device. To this end, a person skilled in the art will provide software on the device, which processes and evaluates the operating parameter values as desired.

If a deviation or a fault is determined following the switch-off and during the second self-diagnosis, it is still possible to react thereto before the device is put into operation again, by virtue of the device being reset or serviced. A surprising deviation only following the switch-on of the device is avoided where possible, and so the device can be put into the operating state and used as planned. This is of particular importance in operating theaters so as not to disturb timings or prevent an operation because no alternative device is available.

By way of example, the device can check during the first and second self-diagnosis as to whether an internal supply or reference voltage has deviations from the target value and whether the reliable operation of the device is still rendered possible. Alternatively, the flow of a device-internal cooling airflow could be measured in order to determine deviations that would have as a consequence an unwanted heating of the device. It is also possible to measure an amount of energy produced in RF current, ultrasonic or laser applications, and to monitor these for deviations from the target value.

In one configuration of the technology, a captured deviation of the operating parameter from the set target value within a value range is stored by the device as a tolerance and a deviation outside of the value range is stored by the device as a fault, wherein the first self-diagnosis is based on a first value range and the second self-diagnosis is based on a second value range and the second value range is smaller than the first.

Here, once again, storing can be implemented in a memory in the device itself or in a memory of a connected component or controller. As described above, software may be available on the device, said software undertaking an evaluation of the measured values of the operating parameter and determining whether a deviation from the target value still lies within or is already outside of the value range. Here, the value range is a range of possible values assumable by the operating parameter, which comprises the target value and which should count as tolerable. The result of this evaluation is stored as a fault if the deviation lies outside of the value range, or it is stored as a tolerance if it lies within the value range. This can relate to a fault value and a tolerance value or a more detailed result, which corresponds to a fault or a tolerance as defined herein. For further evaluations, software can access the memory and read the value.

Moreover, a larger value range for tolerable deviations is now assumed during the first self-diagnosis following switch-on than during the second self-diagnosis following switch-off. Thus, the second self-diagnosis is based on a tighter or smaller value range for permitted deviations of the operating parameter around the target value, and hence a stricter measure is applied to the permitted deviation than in the case of the first self-diagnosis. In general, the value range may also correspond to only a single target value. The second value range can be less than the first value ranges by at least 25% and, in particular, by at least 50%. Here, the size of the range relates to the difference between a maximum value and a minimum value of the respective value range. The value ranges comprise the target value; however, the smaller second value range need not be completely contained within the first larger value range.

Advantageously, this facilitates the operation of the device even in the case of relatively large deviations of the values following the first diagnosis. Only a smaller value range is permitted upon switch-off, and hence only less-severe deviations are not stored as a fault. Expressed differently, even relatively small deviations now lead to a fault. Following the operation of the device, the user can react thereto and remedy the fault before said device should be put into operation again so that the device is then available in a proper working state.

The smaller, second value range for the second self-diagnosis is moreover advantageous in that deviations of the measured values from the target value of the operating parameter caused by changing ambient conditions during the operation of the device can be taken into account and can be compensated for. By way of example, if the device has heated during operation and this heat has had an effect on the measurement electronics of the sensors, it may be the case of values of the operating parameter such as voltage or pressure no longer correspond to the values actually present. The measured values deviate or are slightly faulty, and so, for safety reasons, it is advantageous to admit a smaller tolerance, i.e., base the second self-diagnosis on a smaller value range, such that entirely inadmissible values of the operating parameter are registered as a fault in any case. This also occurs if the sensors no longer measure reliably or indicate values deviating from reality. The expected deviations are taken into account by the smaller value range. In particular, this is possible if the behavior of the sensors under modified operating conditions is known.

The effects of a determined fault during the first self-diagnosis and/or during the second self-diagnosis can be set to be different depending on the operating parameter, for example by software on the device as will still be described in more detail below.

An acoustic or optical warning can be generated in the case where a fault is stored during the self-diagnosis. The device itself can generate the warning. Alternatively, the stored fault can be communicated to a further device or connected component, and the warning can be generated thereby. The optical warning can be a light such as an activated light-emitting diode, a flashing light or else an indication on a display, such as text. An acoustic warning can be implemented as a sound or as speech output, generated by the device or the connected component. To this end, the device can have a loudspeaker.

If the measured deviation of the operating parameter from the value range is so large that a fault is stored, the user's attention is drawn thereto with the aid of the generated warning. Depending on the relevance of the deviation or the malfunction, this can be implemented immediately, when the device is switched off or after a renewed switch-on. The warning allows the user to react to the deviation or the fault and, where necessary, take up measures to remedy this. This can prevent a faulty function of the device having an effect on the user or the patient. By way of example, this can prevent overheating of a device or a surge.

The warning can be generated if the first self-diagnosis determines a fault, if the second diagnosis determines a fault or only if both diagnoses determine a fault for the relevant operating parameter. This may also depend on the relevance of the parameter and the affected components and functions for the application. When selecting these options, a person skilled in the art will take account of the fact that, according to the problem addressed, a reliable operation of the device should firstly be ensured and that, secondly, it should be possible to react to faults at the right time during the operation of the device.

In general, there can be a plurality of measurements of an operating parameter both during the first and during the second self-diagnosis, or a plurality of sensors can determine the same parameter value.

In the case of devices and additional components such as foot pedals, monitors and the like, which are interconnected by way of signal lines, wireless connections, BUS systems or the like, the first and second self-diagnosis may also comprise operating parameters of these further devices and components.

In one configuration of the technology, the warning is generated following a further switch-on and prior to a further first self-diagnosis of the device. If a fault was stored in the preceding operation of the device during the first or second diagnosis, this can also be communicated to the user as a warning following a renewed switch-on.

Advantageously, the warning can also comprise a notification for the user at the same time. That is to say, it can provide the user with a notification as to how the indicated fault should be dealt with. This can be implemented by way of an audio communication, as text on a display or by an optical or acoustic signal with a defined meaning, as provided in the instructions, for example. The notification can provide the user with instructions as to how the fault is remedied.

A stored fault determined during the first and/or second self-diagnosis may lead to the device not being put into the operating state after a renewed switch-on. In extremis, this can prevent the faulty device from being used and endangering the patient or user.

In a further configuration, and possibly depending on the relevant operating parameter, the warning is only generated in the case where a fault is stored in the first and the second self-diagnosis. This can ensure that a fault is in fact present and the cause has not already disappeared again, for instance during the operating state.

As an alternative or in addition thereto, a warning can be generated in the case where a tolerance is stored in the first self-diagnosis and a fault is stored in the second self-diagnosis. A fault stored after the switch-off and during the second self-diagnosis allows the user to react to the fault without interrupting the course of the treatment. In the case where the second self-diagnosis is based on a smaller value range for the deviation of the operating parameter, it will often be the case that a value after switch-on will still lie within the greater value range but will lie outside the tighter value range of the second diagnosis after switch-off, even if the value has not changed during operation, and thus generate an error. The user can in turn react to the fault at this time.

In order to ensure that the user also takes note of a fault, provision can be made for the device to not immediately terminate the operating state following the switch-off in the case where a fault is stored in the first or second self-diagnosis or in both self-diagnoses. In particular, a warning is generated and displayed. The operating state is only terminated once there has been a suitable reaction to the fault.

It is an aspect of the present technology that the device performs a self-diagnosis only after switch-on and after switch-off, but not in an idle state following the termination of the operation.

A method according to the technology for operating a medical device comprises the steps of:
switching-on the device,
performing a first self-diagnosis, in which at least a first operating parameter is checked for a deviation from a target value of the operating parameter,
activating the device and putting the device into an operating state,
switching-off the device,
performing a second self-diagnosis, in which at least the first operating parameter is checked for a deviation from a target value of the operating parameter,
terminating the operating state.

In one configuration of the method, a deviation of the operating parameter from the set target value within a value range is stored by the device as a tolerance and a deviation outside of the value range is stored by the device as a fault, wherein the first self-diagnosis is based on a first value range and the second self-diagnosis is based on a second value range and the second value range is smaller than the first.

Following the step of performing the second self-diagnosis, the method may comprise the additional step of generating an optical or acoustic warning in the case where a fault is stored following the second self-diagnosis.

Moreover, all further above-described possible aspects of a medical device according to the technology can also be aspects of the device operated by the method described herein.

BRIEF DESCRIPTION OF THE DRAWINGS

Further aspects of the technology arise from the following description of the preferred exemplary embodiments and the attached drawings. In the drawings.

DETAILED DESCRIPTION

Figure 1:
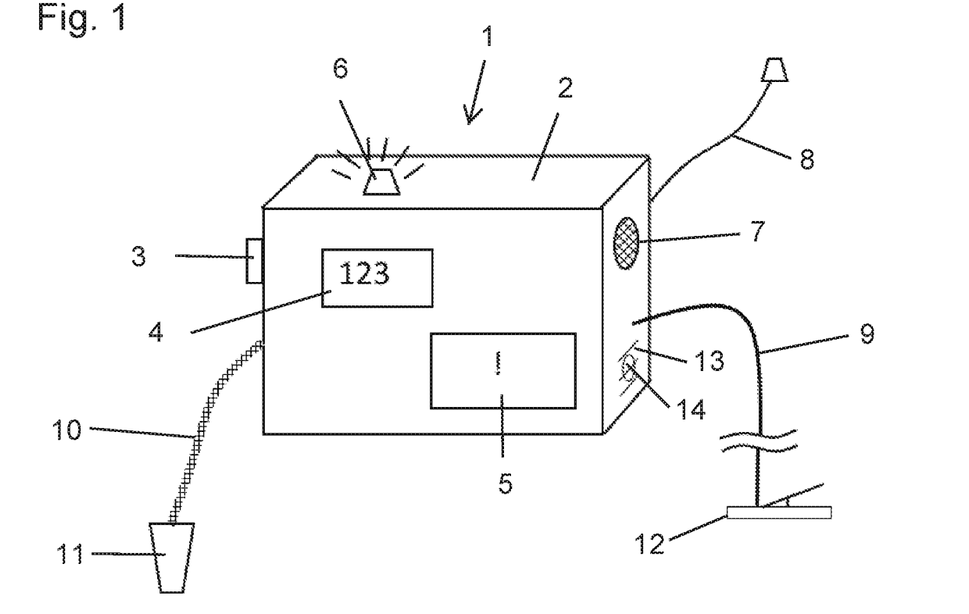
FIG. 1 shows an exemplary embodiment of a medical device according to the technology.

A medical device 1 illustrated in FIG. 1 comprises a housing 2 and an on and off switch 3 in the form of a pushbutton, which is located on the housing 2. An indication means 4, for indicating a set pressure, and a display 5 are located on a front surface of the housing. A light-emitting diode 6 is situated on the top of the housing 2 and a loudspeaker 7 is disposed on a side of the housing 2. By way of a power cable 8, the device 1 is connected to a socket, not illustrated, which provides a mains voltage. A signal line 9 connects the device 1 to an input device in the form of a foot pedal 12. On the opposite side of the housing 2, a fluid line 10 in the form of a tube is connected to the device 1. The fluid line 10 leads to a trocar 11. In the present exemplary embodiment, the device 1 is an insufflator, which can provide a patient with an insufflation gas, for example $CO_2$, via the fluid line 10 and the trocar 11. To this end, the gas is introduced under pressure into the body of a patient from the insufflator 1 via the line 10 and the trocar 11, for example in order to expand an abdominal cavity for an endoscopic operation. To this end, the trocar 11 is introduced into the abdominal wall of the patient.

Figure 2:
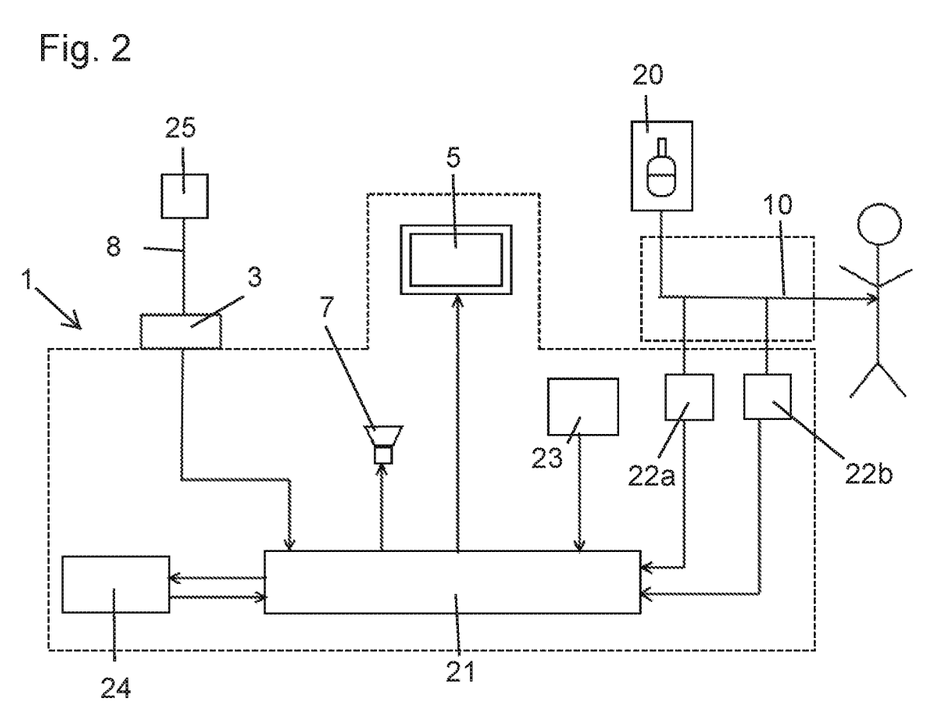
FIG. 2 shows a block diagram of a medical device according to the technology.

FIG. 2 shows a schematic circuit diagram of the device 1. The device 1, the housing 2 of which is indicated by the dashed lines, comprises a controller in the form of a microcontroller 21 and two sensors 22a and 22b, which measure and regulate a pressure in the line 10 between the gas flask 20, device 1 and patient in order to avoid excess pressure in the patient. Excess pressure would put the safety of the patient at risk. By way of example, closed-loop control is implemented by way of a pressure controller, not illustrated here, which is connected to the line 10 and likewise controlled by the microcontroller 21. The target pressure either specified by the device 1 or set by the user is indicated to the user on the display 4. The sensors 22a and 22b are assembled together with other electronic components on a circuit board, not illustrated, within the housing 2. The device 1 heats up during operation, as a result of which the temperature within the housing 2 increases. The electronic components and the sensors 22a,b must be protected from overheating as they would otherwise no longer operate correctly and could provide incorrect measured values. A target temperature Tsoll is specified for the device 1 by software which runs on the microcontroller 21 of the device 1. Therefore, the circuit board also has a temperature sensor 23, which measures the temperature within the housing 2. The controller 21 of the device 1 also monitors this measured value.

The user activates the device 1 via the switch 3, as a result of which the power supply is established from a power source 25 to the device 1 via the power cable 8. The device 1 performs a first self-diagnosis immediately after switch-on. In the process, various operating parameters of the device 1 are checked by the latter, including the temperature T in the housing interior measured by the temperature sensor 23.

Figure 3:
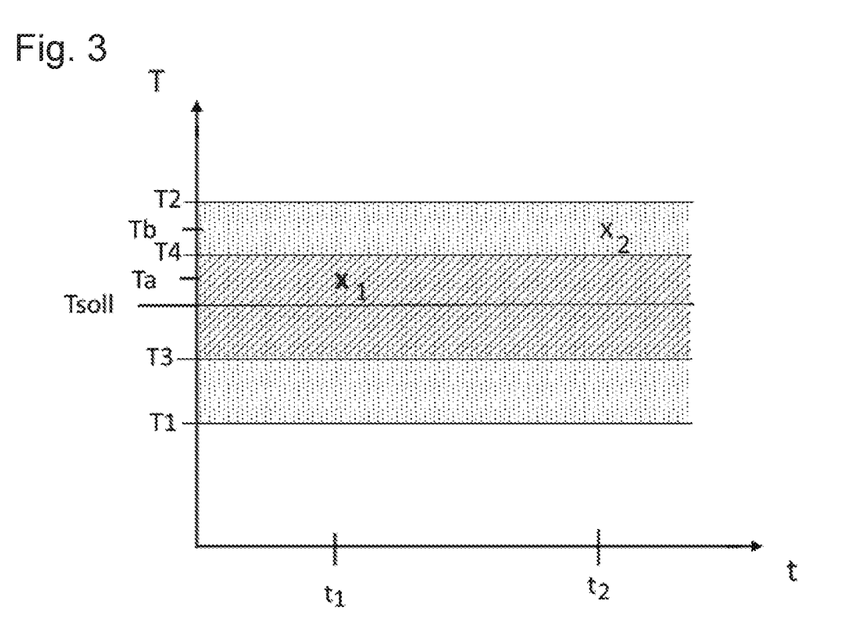
FIG. 3 shows a diagram of measured values of the first and second self-diagnosis, and a first and second value range.

FIG. 3 illustrates the result of the temperature measurement. At a time t1, the first measurement is carried out within the scope of the first self-diagnosis and a value Ta is ascertained for the interior temperature. This value lies above the target temperature Tsoll but within a first value range, illustrated using dots, with a lower limit T1 and an upper limit T2. The controller 21 of the device 1 evaluates the measurement result within the scope of the first self-diagnosis and compares the first measured value Ta with the specified first value range. This value range represents the range within which deviations from the target temperature Tsoll can be accepted as they are no immediate risk to the electronic components. The controller 21 of the device 1 stores the result of the measurement as a value lying within the tolerance in a memory 24. Since no fault is present, the device 1 is put into an operating state and is available to the user. A gas supply to the patient can now be triggered by the user via the foot pedal 12 as required.

Following the termination of the medical intervention, the device 1 is switched off by the user via the switch 3. The device 1 performs a second self-diagnosis at this time t2 and checks, inter alia, the temperature in the housing 2 again. As is evident from FIG. 2, the measured value Tb now lies above the measured value Ta at the start of the intervention. The device 1 has heated up during running operation. The second self-diagnosis is based on a second value range for the temperature T, hatched in the diagram, with a minimum temperature T3 and a maximum temperature T4. This range is smaller than the first value range; in particular, the maximum temperature T4 lies below the maximum temperature T2 of the first value range. The measured temperature Tb within the device 1 no longer lies within the second value range, but thereabove. Therefore, the controller 21 determines a non-tolerable deviation of the temperature T from the target temperature Tsoll and stores the value as a fault in the memory 24.

Figure 4:
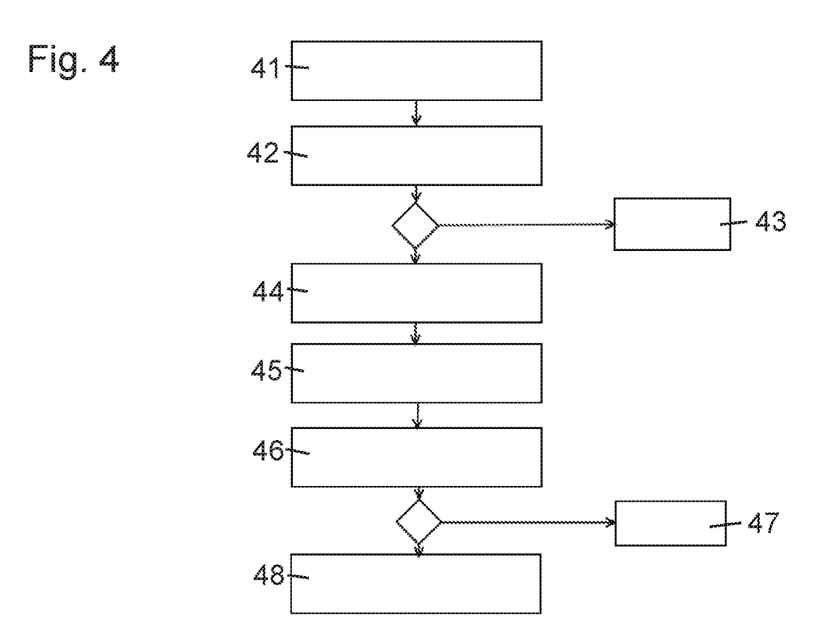
FIG. 4 shows a diagram of a method according to the technology.

FIG. 4 illustrates, by way of example, the progression of the method according to the technology. It starts with the switch-on step 41, whereupon the step of the 1st self-diagnosis 42 of the device 1 is implemented. Two cases may occur here: either a fault is determined and stored in the memory 24 in the next step 43 or there is no fault, which is why the device 1 transitions into the operating state in the next step 44.

After the termination of a medical intervention, the device 1 is switched off in the next step 45, which is followed by the 2nd self-diagnosis 46. Here, too, two cases may occur again and either a fault is stored in the next step 47 or the operating state is terminated in the final step 48.

Assume that a fault has been stored during the second self-diagnosis in the present case. To inform the user about the fault, a sound is generated by the loudspeaker 7 and the light-emitting diode 6 lights up as a warning in a further step of the method that precedes step 48. Text with the notification that the device 1 has heated up too strongly appears on the display 5. The notification moreover suggests the user ensure that the cooling slots 13 on the housing 2 are not covered and the device 1 is not switched on again for a period of time of 15 minutes so that it can cool down. Following the completion of the second self-diagnosis 46, the operating state of the device 1 is not terminated immediately; instead, the device 1 and, in particular, the fan 14 continue to run for another five minutes in order to lower the internal housing temperature more quickly and avert damage to the electronic components. Only then is the device 1 finally switched off and the connection to the mains current 25 is interrupted.

In an alternative embodiment, the device 1 is embodied as described above and connected to the further components 11, 12 and the gas flask 20; however, it does not have a temperature sensor for measuring the temperature in the housing 2 of the device 1. Instead, the pressure P1 applied to the line 10 is captured by the pressure sensors 22a and b during the first self-diagnosis. If the measured values of the pressure P1 lie within a first value range around the pressure target value Psoll, the device 1 is activated and put into the operating state. Following the end of the medical intervention, the device 1 is switched off again and the second self-diagnosis is thereupon performed by the device 1 itself. The device 1 is known to heat up during the operation and the elevated temperature in the device 1 is known to have an effect on the measurement results of the pressure sensors 22a and b. Now, the pressure P2 in the line 10 is measured by the pressure sensors 22a,b during the second self-diagnosis and a second, smaller value range around the target value of the pressure Psoll is used during the evaluation of the measured values. This smaller second value range is stored in the device controller 21 and sets a tighter boundary than the first value range for the allowed values of the pressure P2, which are intended to be tolerated. What is consequently taken into account is that pressure values measured by the heated pressure sensors 22a and b do not always correspond to the actual pressure values in the line 10 on account of a thermally caused influence on the electronics. For safety reasons, a stricter measure is applied to the pressure values to be tolerated and this decides whether a fault or tolerance is present during the evaluation of the measured values in the controller 21. Depending on the measurement result, the device 1 can then be deactivated or a warning can be output, as described above.

LIST OF REFERENCE SIGNS

1 Medical device
2 Housing
3 Switch

4 Indication means
5 Display
6 Light-emitting diode
7 Loudspeaker
8 Power cable
9 Signal line
10 Fluid line
11 Trocar
12 Foot pedal
13 Cooling slots
14 Fan
20 Gas flask
21 Microcontroller
22a, b Pressure sensors
23 Temperature sensor
24 Memory
25 Power source
41 Switch-on
42 First self-diagnosis
43 Storing a fault
44 Activating an operating state
45 Switch-off
46 Second self-diagnosis
47 Storing a fault
48 Terminating the operating state
t1 Time of the 1st self-diagnosis
t2 Time of the 2nd self-diagnosis
Tsoll Temperature target value
T1 Minimum first value range of the temperature
T2 Maximum first value range of the temperature
T3 Minimum second value range of the temperature
T4 Maximum second value range of the temperature
Ta First measured value
Tb Second measured value

The invention claimed is:

1. A medical device comprising: one or more switches configured to turn the device on and off, wherein a turning on of the device by the one or more switches activates the device and puts the device into an operating state, and a turning off of the device by the one or more switches deactivates the device and terminates the operating state, wherein the device in the operating state carries out at least one safety-relevant function using at least one operating parameter with a set target value, and wherein the device is configured to: perform a first self-diagnosis following the turning on of the device by the one or more switches and before reaching the operating state, and perform a second self-diagnosis following the turning off of the device by the one or more switches and before terminating the operating state, during which self-diagnoses the same operating parameter of the at least one operating parameter of the device is checked for deviation from the set target value.

2. The medical device as claimed in claim 1, wherein the deviation of the operating parameter from the set target value within a values range is stored by the device as a tolerance and a deviation outside of the value range is stored by the device as a fault,
wherein the first self-diagnosis is based on a first value range and the second self-diagnosis is based on a second value range, the second value range being smaller than the first.

3. The medical device as claimed in claim 2, wherein the device does not immediately terminate the operating state following the switch-off in the case where a fault is stored.

4. The medical device as claimed in claim 2, wherein the second value range is less than the first by at least 25% and, in particular, by at least 50%.

5. The medical device as claimed in claim 2, wherein an optical or acoustic warning is generated in the case where a fault is stored.

6. The medical device as claimed in claim 5, wherein the warning is generated following a further switch-on and prior to a further first self-diagnosis.

7. The medical device as claimed in claim 6, wherein the device is not put into the operating state.

8. The medical device as claimed in claim 5, wherein the warning comprises a notification for the user of the device.

9. The medical device as claimed in claim 5, wherein the warning is only generated in the case where a fault is stored in the first and the second self-diagnosis.

10. The medical device as claimed in claim 5, wherein the warning is generated in the case where a tolerance is stored in the first self-diagnosis and a fault is stored in the second self-diagnosis.

11. The medical device as claimed in claim 1, wherein the operating parameter is a voltage, a current intensity, a fluid flow, a pressure, an amount of luminous energy or a temperature.

12. The medical device as claimed in claim 7, wherein there is no self-diagnosis in the deactivated state of the device.

13. The medical device of claim 7, wherein the one or more switches include a touchscreen.

14. The medical device of claim 7, wherein the one or more switches include speech input into a microphone, a switch on a central control unit or a switch on another separate input device.

15. The medical device of claim 7, wherein the one or more switches are turned on based on an operating state of another device.

16. The medical device of claim 7, wherein the one or more switches include a pressure switch or lever.

17. A method for operating a medical device, including the steps of: switching-on the device, performing a first self-diagnosis, in which at least a first operating parameter is checked for a deviation from a target value of the operating parameter, activating the device and putting the device into an operating state, switching-off the device, performing a second self-diagnosis after the switching off of the device and before terminating the operating state, in which at least the first operating parameter is checked for a deviation from the target value of the operating parameter, and terminating the operating state.

18. The method as claimed in claim 17, wherein the deviation of the operating parameter from the target value within a value range is stored by the device as a tolerance and the deviation outside of the value range is stored by the device as a fault, wherein the first self-diagnosis is based on a first value range and the second self-diagnosis is based on a second value range, the second value range being smaller than the first.

19. The method as claimed in claim 18, additionally including the step of generating an optical or acoustic warning in the case where a fault is stored following the second self-diagnosis.

20. A medical device comprising: a microprocessor and memory; and one or more switches, the one or more switches configured to turn the device on and off, wherein: a turning on of the device by the one or more switches activates the device and places the device into an operating state, and a turning off of the device by the one or more switches deactivates the device and terminates the operating state, wherein the device when in the operating state carries out at least one safety-relevant function using at least one operating parameter with a set target value, and wherein the device in conjunction with the microprocessor and memory is configured to: perform a first self-diagnosis following the turning on of the device by the one or more switches and before reaching the operating state, and perform a second self-diagnosis following the turning off of the device by the one or more switches and before terminating the operating state, wherein during the first self-diagnosis and the second self-diagnosis the same operating parameter of the at least one operating parameter of the device is checked for deviation from the set target value stored in the memory.

* * * * *